US012773380B2

(12) United States Patent
Oliva et al.

(10) Patent No.: US 12,773,380 B2
(45) Date of Patent: Oct. 27, 2026

(54) COSMETIC COMPOSITION BASED ON BIOSOURCED ISODODECANE AND PREPARATION METHOD THEREOF

(71) Applicant: GLOBAL BIOENERGIES, Evry (FR)

(72) Inventors: Luisa Oliva, Neuilly sur Seine (FR); Marc Delcourt, Paris (FR)

(73) Assignee: GLOBAL BIOENERGIES, Evry (FR)

( * ) Notice: Subject to any disclaimer, the term of this patent is extended or adjusted under 35 U.S.C. 154(b) by 694 days.

(21) Appl. No.: 17/924,983

(22) PCT Filed: May 11, 2021

(86) PCT No.: PCT/EP2021/062433

§ 371 (c)(1),
(2) Date: Nov. 11, 2022

(87) PCT Pub. No.: WO2021/228824

PCT Pub. Date: Nov. 18, 2021

(65) Prior Publication Data

US 2023/0181432 A1 Jun. 15, 2023

(30) Foreign Application Priority Data

May 14, 2020 (FR) ....................................... 2004769

(51) Int. Cl.

*A61K 8/31* (2006.01)
*A61Q 1/06* (2006.01)
*A61Q 1/08* (2006.01)
*A61Q 1/10* (2006.01)
*A61Q 1/14* (2006.01)

(52) U.S. Cl.

CPC .................. *A61K 8/31* (2013.01); *A61Q 1/06* (2013.01); *A61Q 1/08* (2013.01); *A61Q 1/10* (2013.01); *A61Q 1/14* (2013.01); *A61K 2800/43* (2013.01); *A61K 2800/85* (2013.01)

(58) Field of Classification Search

None
See application file for complete search history.

(56) References Cited

U.S. PATENT DOCUMENTS

2011/0172475 A1 7/2011 Peters et al.
2015/0329878 A1* 11/2015 Bockrath ................. C12N 1/20 435/167

FOREIGN PATENT DOCUMENTS

| | | | |
|---|---|---|---|
| EP | 1 716 888 | 11/2006 | |
| FR | 3 031 300 | 7/2016 | |
| WO | 2010/001078 | 1/2010 | |
| WO | 2011/032934 | 3/2011 | |
| WO | 2012/052427 | 4/2012 | |
| WO | 2014/086781 | 6/2014 | |
| WO | 2016/042012 | 3/2016 | |
| WO | WO-2016110544 A1 * | 7/2016 | ............... A61Q 1/10 |
| WO | 2017/085167 | 5/2017 | |
| WO | 2018/206262 | 11/2018 | |

OTHER PUBLICATIONS

Van Leeuwen et al., "Fermentative production of isobutene," Applied Microbiology and Biotechnology, 2012, vol. 93, pp. 1377-1387.
Follonier et al., "Pressure to kill or pressure to boost: a review on the various effects and applications of hydrostatic pressure in bacterial biotechnology," Applied Microbiology and Biotechnology, 2012, vol. 93, pp. 1805-1815.
Littich et al., "Bio-based alternatives for silicone and petrochemical emollients from natural oil metathesis," Household and Personal Care Today, vol. 9, No. 3, May/Jun. 2014, pp. 18-20.
Lui Sha, "Using Simplicity to Control Complexity," IEEE Software, vol. 18, No. 4, Jul. 1, 2001, pp. 20-28.
Anonymous, "Global Bioenergies: release of the first batch of cosmetic-grade renewable isododecane," https://www.global-bioenergies.com/release-of-the-first-batch-of-cosmetic-grade-renewable-isododecane/?lang=en, Jan. 14, 2021, 2 pages.
International Search Report dated Aug. 9, 2021, for PCT/EP2021/062433, 6 pages.
Written Opinion of the ISA dated Aug. 9, 2021, for PCT/EP2021/062433, 11 pages.
French Search Report dated Jan. 18, 2021, for FR 2004769, 2 pages.
Rocle, "Direct Fermentation to Renewable isobutene, a platform to fuels and chemicals" www.asprom.com/biotech/rocle.pd, Oct. 1, 2018, 22 pages.

* cited by examiner

*Primary Examiner* — Nicole P Babson
(74) *Attorney, Agent, or Firm* — NIXON & VANDERHYE

(57) ABSTRACT

Disclosed is a method for preparing a cosmetic composition including the preparation of isododecane of natural origin and the mixture of isododecane formed with at least one compound selected from among: waxes, oils, film-forming agents, dyes and mixtures thereof. Also disclosed is the resulting cosmetic composition.

3 Claims, No Drawings

COSMETIC COMPOSITION BASED ON BIOSOURCED ISODODECANE AND PREPARATION METHOD THEREOF

CROSS-REFERENCE TO RELATED APPLICATIONS

This application is the U.S. national phase of International Application No. PCT/EP2021/062433 filed May 11, 2021 which designated the U.S. and claims priority to FR 2004769 filed May 14, 2020, the entire contents of each of which are hereby incorporated by reference.

BACKGROUND OF THE INVENTION

Field of the Invention

The present invention relates the preparation method for a cosmetic composition containing biosourced isododecane. The invention further relates to a cosmetic composition which can be obtained using the method according to the invention.

Description of the Related Art

A large number of chemical compounds are currently derived from petrochemicals. Alkanes e.g. are nowadays commonly used in many economic sectors, such as energy (fossil energy) or as raw materials for the synthesis of complex products (plastics, detergents, etc.).

Among alkanes, isododecane is of particular interest. For the energy sector e.g. isododecane is one of the few molecules likely to be an alternative fuel for aviation. Isododecane is also used as an organic solvent for chemical synthesis, pigment dispersion, the preparation of plant-protection products or further as a heat transfer fluid. Finally, isododecane is of significant interest for the cosmetics industry where same is now widely used for the solvent role thereof and the emollient properties thereof.

The name "isododecane" covers all branched alkanes with 12 carbon atoms, one of the most widely used of which is 2,2,4,6,6-pentamethyheptane. Alkanes such as isododecane are currently produced by distillation of crude oil. Production costs are thus closely linked to the price of oil. Since oil resources are limited, such synthetic routes do not provide a sustainable and environmentally friendly way of producing isododecane.

The biological production of alkanes such as isododecane is nowadays necessary within the framework of sustainable industrial exploitation in harmony with geochemical cycles. For the cosmetics industry, the production of alkanes by biological means is of strategic interest for the preparation of compositions with an ever higher content of natural compounds.

Fermentative production methods play an important role in the supply of various hydrocarbons and are often an important alternative to chemical methods. As the operating costs of fermentation methods can be high, it is constantly necessary to provide more cost-effective methods. Attempts to reduce operating costs include e.g. the development of recombinant organisms which use a metabolic route for the production of the desired compound, which results in reduced energy consumption, the development of enzymes with higher activity, the use of cheaper substrates and others. Over the past decade, attempts to produce hydrocarbon compounds of interest for industry (e.g. as biofuels or as polymer components) using fermentation methods have increased and, in the meantime, various enzymatic reactions for the production of such compounds in microorganisms have been described. The development of corresponding fermentation methods poses specific problems thereof because same often involve completely new metabolic routes involving unusual enzymatic conversions. The production by fermentation of certain hydrocarbons is described e.g. in van Leeuwen B N et al, Appl Microbiol Biotechnol, 2012, 93 (4): 1377-1387 and in WO 2012/052427. The development of a fermentation method requires the development of specific conditions, in particular in terms of temperature, pressure and air flow, which are adjusted according to the target product and the producing microorganism. Such parameters have been the subject of several studies, in particular Follonier S et al, Appl Microbiol Biotechnol, 2012, 93 (5): 1805-1815 relating to the pressure at the fermenter.

WO 2014/086781 teaches a method for the preparation of hydrocarbons, isobutene in particular, by fermentation.

WO 2017/085167 discloses a method for the production of isobutene by the enzymatic conversion of 3-methylcrotonic acid to isobutene, 3-methylcrotonic acid being as such obtained by the succession of enzymatic reactions starting from acetyl-CoA.

The applicant has henceforth discovered that it is possible to synthesize isododecane suitable for the preparation of cosmetic compositions, from natural isobutene.

In particular, the method developed by the Applicant can be used for preparing isododecane, the level of purity and isomeric selectivity of which makes possible the use thereof in cosmetic compositions.

SUMMARY OF THE INVENTION

The invention first relates to a preparation method for a cosmetic composition, comprising the following steps:

1) producing isobutene by a fermentation method comprising the formation of 3-hydroxy-3-methylbutyric acid and/or 3-methylcrotonic acid as an intermediate substance,
2) converting isobutene to isododecane, and
3) mixing isododecane with at least one compound selected from: waxes, oils, resins, dyes and mixtures thereof.

Preferentially, step 2) for converting isobutene to isododecane is carried out by oligomerization of isobutene, followed by a hydrogenation step.

Preferentially, the oligomerization step is carried out at a pressure ranging from 10 to 30 bars.

Preferentially, the oligomerization step is carried out at a temperature ranging from 50 to 150° C.

Advantageously, the method according to the invention further comprises a distillation step, either before or after the hydrogenation step, preferentially after the hydrogenation step.

The invention further relates to a cosmetic composition which can be obtained by the method defined above and detailed hereinafter.

Preferentially, the cosmetic composition according to the invention comprises from 2 to 80% by mass of base oils with respect to the total mass of the composition.

Preferentially, the isododecane present in the composition according to the invention has a percentage of modern carbon (PMC), determined as per the ASTM standard D6866-20 Method B, greater than or equal to 50%, preferentially greater than or equal to 60%, more preferentially greater than or equal to 70%, advantageously greater than or equal to 80%, typically greater than or equal to 90%.

Advantageously, 100% of the isododecane present in the composition according to the invention is biosourced and has a percentage of modern carbon (PMC), determined as per the standard ASTM D6866-20 Method B, equal to 100%.

Advantageously, the cosmetic composition according to the invention comprises:

from 2 to 80% by mass of isododecane,
from 2 to 60% by mass of wax(es)
from 1 to 40% by mass of oil(s)
from 2 to 40% by mass of film-forming agent(s), and
from 0 to 30% by mass of dye(s),
the percentages being expressed with respect to the total mass of the composition.

According to an advantageous embodiment, at least 80% by mass of the compounds present in the cosmetic composition according to the invention are natural, preferentially at least 90% by mass, more preferentially at least 95% by mass, with respect to the total mass of the composition.

Preferentially, the cosmetic composition according to the invention has a percentage of modern carbon (pMC), determined as per the ASTM Standard D6866-20 Method B, greater than or equal to 65%, more preferentially greater than or equal to 75%, even more preferentially greater than or equal to 80%, typically greater than or equal to 85%.

Advantageously, the cosmetic composition according to the invention has a percentage of modern carbon (pMC), determined as per the ASTM standard D6866-20 Method B, greater than or equal to 90%, more advantageously greater than or equal to 95%.

According to one embodiment, the composition further comprises from 1 to 40% by mass of butter(s), with respect to the total mass of the composition.

Preferentially, the composition consists of a foundation; a mascara; a solid or liquid eyebrow mascara; an eyebrow pencil; a blusher; a corrector; a solid or liquid lipstick; an eyeshadow; an eyeliner; a primer, in particular a pearly primer or a make-up removing oil.

Advantageously, the cosmetic composition according to the invention has a resistance over time greater than or equal to 6 hours, preferentially greater than or equal to 8 hours.

DESCRIPTION OF THE PREFERRED EMBODIMENTS

The invention first relates to a method for the preparation of a cosmetic composition based on biosourced isododecane.

"Biosourced product" or natural product as defined by the invention, refers to a chemical product obtained from renewable raw materials coming from biomass.

Natural or biosourced isododecane differs from isododecane coming from petroleum (fossil) by the concentration thereof of carbon 14. Since biosourced isododecane comes from the conversion of organic matter and same has a high concentration of carbon 14. By contrast, isododecane coming from petroleum has a low, or even zero, concentration of carbon 14.

Hereinafter in the application, the concentration of carbon 14 in isododecane is evaluated by determining the percentage of modern carbon thereof.

Modern carbon is the contemporary carbon present today in the atmosphere and in biomass. Radiocarbon measurement is expressed in parts of modern carbon (PMC). The percentage of biosourced carbon is calculated based on the PMC, the total concentration of carbon and an atmospheric correction factor (REF). The reference value used for the carbon year correction in 2020 was 100 (ASTM D6866-20). Thus, a 100% natural product manufactured in 2020 has a PMC of 100.

The percentage of modern carbon corresponds to the percentage of "natural" carbon (coming from biomass) compared to "fossil" carbon (coming from petrochemistry). A compound having a concentration of modern carbon of 100% is made from 100% of plants and/or animal by-products. A concentration of modern carbon of 0% is associated with a product which comes entirely from a fossil source, which contains no carbon coming from plants and/or animal by-products.

A PMC value greater than 0% and less than 100% confirms a mixture of biosourced and fossil carbon, indicating the percentage of biosourced carbon in the total carbon.

The method according to the invention comprises the following steps:

1) producing isobutene by a fermentation method,
2) converting isobutene to isododecane, and
3) mixing isododecane with at least one compound selected from: waxes, oils, resins, dyes, and any mixtures thereof.

The method according to the invention comprises a first step of producing isobutene (2-methylpropene according to the IUPAC name) by a fermentation method.

The fermentation method is typically carried out from renewable resources (sugar, cereals, forest and agricultural waste). The carbohydrates obtained from such renewable resources are introduced into the fermentation medium.

The fermentation method comprises the succession of a plurality of enzymatic conversion steps, one of the intermediate products of which is acetyl-CoA.

Preferentially, acetyl-CoA is obtained by enzymatic conversions of sucrose and/or glucose.

Advantageously, the fermentation method comprises a step of forming 3-hydroxy-3-methylbutyric acid and/or 3-methylcrotonic acid as an intermediate substance.

According to a first variant, the fermentation method comprises an intermediate step of preparing 3-hydroxy-3-methylbutyric acid, also known as 3-hydroxyisovaleric acid.

Methods for converting acetyl-CoA to 3-hydroxy-3-methylbutyric acid typically include a step of preparing 3-methylcrotonyl-CoA followed by a step of conversion into 3-methylcrotonic acid. A hydration step can then be used for changing from 3-methylcrotonic acid to 3-hydroxy-3-methylbutyric acid.

The preparation of isobutene from 3-hydroxy-3-methylbutyric acid is then carried out by the succession of a phosphorylation step and a decarboxylation/dephosphorylation step.

Methods and recombinant microorganisms using such routes have been described in particular in WO 2010/001078, WO 2012/052427, WO 2011/032934 and WO 2016/042012.

According to a second variant, the fermentation method comprises an intermediate step of preparing 3-methylcrotonic acid, also called 3-methyl-2-butenoic acid, 3,3-dimethylacrylic acid or senecioic acid.

Enzymatic methods for the production of 3-methylcrotonic acid from acetyl-CoA comprise the preparation of 3-methylcrotonyl-CoA as an intermediate substance.

According to an alternative embodiment, 3-methylcrotonic acid is obtained by the conversion of 3-hydroxy-3-methylbutyric acid, the synthesis of which has been described hereinabove.

The preparation of isobutene from 3-methylcrotonic acid is then carried out by enzymatic decarboxylation. The step of decarboxylation of 3-methylcrotonic acid can be carried out in particular in the presence of an FMN-dependent decarboxylase, combined with a flavin mononucleotide (FMN) phenyl transferase, wherein said FMN phenyl transferase catalyzes the phenylation of an FMN cofactor or flavin adenine dinucleotide (FAD) cofactor using dimethylallyl phosphate (DMAP) or dimethylallyl pyrophosphate (DMAPP).

Methods and recombinant microorganisms using such routes have been described in particular in WO2017/085167 and WO2018/206262.

The present invention is not limited to such major reactions but further relates to all the other routes and the individual steps of the conversion of acetyl-CoA into isobutene as described in the prior art documents WO 2017/085167, WO 2018/206262, WO 2010/001078, WO 2012/052427, WO 2011/032934, WO 2016/042012.

Preferentially, the microorganism apt to produce isobutene is cultured in a liquid fermentation medium, the isobutene being obtained in the gaseous state in the fermentation effluent gases.

Advantageously, the production of isobutene is carried out in a fermenter fed with an input gas comprising oxygen.

Preferentially, the total pressure of the input gas before introduction into the fermenter is from about 1.5 bar to about 15 bar, more preferentially from 1.5 bar to about 10 bar, even more preferentially from 3.5 bar to 6 bar.

Preferentially, the partial pressure of oxygen in the input gas, before its introduction into the fermenter, is from 315 mbar to 5.25 bar.

Preferentially, the oxygen concentration in the input gas ranges from 15% to 40% by volume, more preferentially from 21% to 35% by volume.

Preferentially, the partial pressure of carbon dioxide in the input gas, before the introduction thereof into the fermenter, ranges from 52.5 μbar to 1.5 bar.

Advantageously, the input gas consists of a gas mixture comprising nitrogen and from 15% to 40% by volume of oxygen, the concentration of nitrogen and oxygen in the gas mixture together representing 95% by volume or more.

More advantageously, the input gas consists of a gas mixture comprising nitrogen and from 21% to 35% by volume of oxygen, the concentration of nitrogen and oxygen in the gas mixture representing together about 95% by volume or more.

Preferentially, the input gas consists of air at a concentration greater than or equal to about 90% by volume.

Advantageously, the input gas is air.

According to an advantageous embodiment, the input gas consists of a mixture of air and effluents from the recycled residual fermentation gas from which the isobutene has been isolated.

Preferentially, according to such embodiment, the mixture comprises nitrogen, from 15% to 20% by volume of oxygen, and at most 10% by volume of carbon dioxide, wherein nitrogen, oxygen and carbon dioxide together represent at least 95% by volume of the input gas.

Advantageously, the oxygen concentration in the gaseous fermentation effluents is controlled so as to be less than or equal to 10% by volume, preferentially less than or equal to about 8% by volume, more preferentially ranging from 4 to 6% by volume.

According to one embodiment, the oxygen concentration in the fermentation gaseous effluents is controlled by adjusting the flow rate of the input gas and/or by adjusting the rate of stirring of the liquid fermentation medium in the fermenter and/or by adjusting the partial pressure of oxygen in the input gas.

Preferentially, the oxygen consumption by the microorganism is greater than or equal to 30%.

Advantageously, the fermenter is a piston-flow fermenter.

According to an advantageous embodiment, the fermenter comprises at least two Rushton turbine agitators, preferentially all the agitators present in the fermenter are Rushton turbine agitators.

Advantageously, the microorganism is a bacterium, a yeast or a fungus.

More advantageously, the microorganism is *Escherichia coli.*

Advantageously, the liquid fermentation medium is maintained at a temperature ranging from 30° C. to 37° C.

A detailed description of the fermentation method is given in WO 2014/086781.

The second step of the method according to the invention consists of the conversion of the isobutene obtained at the end of step 1) into isododecane.

Preferentially, the conversion of isobutene to isododecane is carried out by oligomerization of isobutene, followed by a hydrogenation step.

Isobutene oligomerization consists of a trimerization step wherein three isobutene monomers react together to form isododecene.

Preferentially, the oligmerization step is carried out under pressure. More preferentially, same is carried out at a pressure ranging from 10 to 30 bars.

Preferentially, during the oligomerization step, the reaction medium is heated. More preferentially, the reaction medium is heated to a temperature ranging from 50 to 150° C.

Advantageously, the oligomerization of isobutene is carried out in the presence of a catalyst.

The catalyst can be chosen from either homogeneous or heterogeneous catalysts, preferentially from heterogeneous catalysts.

Preferentially, the heterogeneous catalyst is chosen from acid resins; modified zeolites, if appropriate; metal oxides and any of the mixtures thereof.

"Modified zeolite" as defined by the invention, refers to a zeolite which has undergone a dealumination step (i.e. treatment with water vapor leading to the migration of aluminum species out of the network) and/or a doping step, in particular with aluminum chloride $AlCl_3$ or iron chloride $FeCl_3$.

When the catalyst is chosen from metal oxides, same is preferentially chosen from zirconia and/or titanium oxides which are optionally sulphated.

Advantageously, the catalyst is chosen from acid resins, in particular from sulphonic resins.

More advantageously, the catalyst is chosen from styrene-divinylbenzene resins functionalized with sulphonic groups.

As styrene-divinylbenzene resin functionalized with sulphonic groups, the range of Amberlyst® resin sold by the company E. I. du Pont de Nemours et compagnie, can be cited as an example.

According to one embodiment, the oligomerization is carried out in the presence of isooctene.

Preferentially, the isooctene is formed in situ, within the reaction medium, by dimerization of isobutene.

Advantageously, at the end of the oligomerization step, the isooctene formed is separated from the reaction medium before being reintroduced into the reactor with the reaction medium of the next batch. The separation of the isooctene is typically carried out by distillation of the reaction medium.

Preferentially, the oligomerization of isobutene is carried out in the presence of an inert solvent, in particular with respect to isobutene, of the catalyst and of the other oligomers formed.

"Inert solvent" as defined by the invention refers to a chemical compound apt to dissolve or dilute a chemical species without reacting with same.

Preferentially, the inert solvent is chosen from either linear or branched C1-C15 alkanes, more preferentially C5-C12 alkanes.

More preferentially, the inert solvent is chosen from branched alkanes.

Advantageously, the inert solvent is chosen from isooctane and isododecane.

According to one embodiment, the oligomerization of isobutene is carried out in a fixed-bed reactor.

Such type of reactor is advantageous in that same makes it possible to dispense with the step of separating the catalyst and the reaction mixture, the catalyst being immobilized on the fixed bed.

Preferentially, the method according to the invention further comprises, following the oligomerization of isobutene, a catalyst recovery step. In the case of a solid catalyst, such step is typically carried out by filtration of the reaction mixture. Other techniques for recovering the catalyst are well known to a person skilled in the art and can be used in an equivalent manner.

At the end of the oligomerization step, the reaction medium consists of a mixture comprising a residual amount of unreacted isobutene and a plurality of alkenes which are oligomers of isobutene, including isododecene.

Preferentially, at the end of the oligomerization step, at least 90 mol % of the starting isobutene was consumed, more preferentially at least 95 mol %, even more preferentially at least 99 mol %, with respect to the total quantity of isobutene initially present in the reaction medium.

Preferentially, isododecene represents at least 70 mol % of the oligomers formed during the oligomerization reaction of isobutene, more preferentially at least 75 mol %, even more preferentially at least 80 mol %, advantageously at least 85 mol %, with respect to the total quantity of oligomers formed.

The method according to the invention further comprises, following the isobutene oligomerization step, a hydrogenation step. Such hydrogenation is used for the conversion of the alkenes present in the reaction medium into alkanes. In particular, it allows the isododecene to be converted into isododecane.

Preferentially, the hydrogenation step is carried out under pressure. More preferentially, same is carried out at a pressure ranging from 10 to 60 bars.

Preferentially, the hydrogenation step is carried out at high temperature. More preferentially, same is carried out at a temperature ranging from 120 to 200° C., preferentially from 140 to 160° C.

Advantageously, the hydrogenation step is carried out in the presence of a catalyst. Any type of catalyst known to a person skilled in the art in hydrogenation reactions can be used, preferentially the catalyst is chosen from metal catalysts.

The catalyst can be chosen from either homogeneous or heterogeneous catalysts, preferentially from heterogeneous catalysts.

When the catalyst is chosen from homogeneous catalysts, same is preferentially chosen from catalysts containing rhodium, iridium, and any of the mixtures thereof. The Wilkinson catalyst and the Crabtree catalyst, respectively, can be cited as an example.

When the catalyst is chosen from heterogeneous catalysts, same is preferentially chosen from catalysts containing palladium, nickel, ruthenium and any of the mixtures thereof. The Lindlar catalyst, Raney nickel and the Grubbs catalyst, respectively, can be cited as an example.

The method according to the invention can further comprise an additional purification step, preferentially by distillation.

Such distillation step can be used for separating the different constituents present in the reaction medium according to the boiling temperature thereof.

The purification step can be carried out either before or after the hydrogenation step.

If implemented before the hydrogenation step, the purification step can be used for separating the different alkenes present in the reaction medium, following the isobutene oligomerization step. Same can be used in particular for isolating isododecene before being able to proceed separately with the hydrogenation thereof into isododecane.

If implemented after the hydrogenation step, the purification step can be used for separating the different alkanes formed during the hydrogenation step. Same can be used in particular for separating isododecane from the other alkanes obtained by hydrogenation of isobutene and the other oligomers thereof.

The implementation of the previous steps is used for the preparation of natural isododecane.

Advantageously, the biosourced isosodecane obtained by carrying out the steps described hereinabove, has a percentage of modern carbon (PMC), determined as per the ASTM standard D6866-20 Method B, equal to 100%.

The percentage of modern carbon in a sample is measured as follows:

The measurements of the different isotopes and the calculations were carried out as per ASTM D6866-20.

The samples are placed as such in an elementary analyzer (Elementar VisION-ISOsel-NCS mode), in order to extract the carbon dioxide $CO_2$. The different isotopes of carbon are separated using a mass spectrometer, and the concentration of $^{14}C$ is determined by comparing the $^{14}C$, $^{13}C$, and $^{12}C$ beams collected simultaneously with same from reference products: oxalic acid (NIST 49900 and IAEA C7) and Kauri wood (IAEA 09). The measurements for controlling the stable isotopic ratios are performed using an IRMS (Isotope-Ratio Mass Spectrometry) spectrometer.

The PMC is calculated according to the method described by Stuiver and Polach (Radiocarbon, 19 (3), 1977, 355-363); the PMC takes into account the correction $\delta^{13}C$ for isotopic fractionation based on the comparison between the concentration measurements of $^{13}C/^{14}C$ and $^{14}C/^{12}C$.

The isododecane obtained preferentially has a purity index greater than or equal to 80% by mass, more preferentially greater than or equal to 90% by mass, even more preferentially greater than or equal to 95% by mass, advantageously greater than or equal to 98% by mass.

The purity index defined above corresponds to the purity of the mixture of all isododecane compounds (branched alkanes having 12 carbon atoms) in the product obtained by implementing the method defined hereinabove.

The isododecane obtained is compatible with a use in a cosmetic composition in that same comprises 2,2,4,6,6-pentamethylheptane as the predominant isomer.

Preferentially, the content of 2,2,4,6,6-pentamethylheptane is greater than or equal to 80% by mass, with respect to the total mass of isododecane obtained.

The method according to the invention finally comprises a step of preparing a cosmetic composition by mixing the isododecane formed with at least one compound chosen from: waxes, oils, resins, dyes and any one of the mixtures thereof.

According to an advantageous embodiment, at least 80% by mass of the compounds present in the composition are natural, preferentially at least 90% by mass, more preferentially at least 95% by mass, with respect to the total mass of the composition.

Advantageously, at least 50% by mass of the compounds present in the composition other than isododecane are natural, preferentially at least 80% by mass, more preferentially at least 90% by mass, advantageously at least 95% by mass, with respect to the total mass of compounds distinct from isododecane and present in the composition.

The method according to the invention can be used for the preparation of all kinds of cosmetic compositions.

The method according to the invention is particularly suitable for the preparation of make-up compositions or make-up removing compositions.

The invention further relates to a cosmetic composition which can be obtained, preferentially obtained, by implementing the method described hereinabove.

"Cosmetic composition" as defined by the invention refers to a composition intended for being brought into contact with the various surface parts of the human body, in particular the face, the epidermis, the hair and scalp systems or further the nails, for the purpose, either exclusively or mainly, to clean same, to perfume same, to change the appearance thereof, to protect same, to keep same in good condition or to correct body odors.

Advantageously, the cosmetic composition according to the invention comprises from 2 to 80% by mass of isododecane with respect to the total mass of the cosmetic composition.

According to an advantageous embodiment, at least 50% by mass of the isododecane present in the cosmetic composition comes from the implementation of the method defined hereinabove, preferentially at least 70% by mass, more preferentially at least 90% by mass, even more preferentially at least 95% by mass.

Preferentially, according to such advantageous embodiment, the isododecane present in the cosmetic composition of the invention has a percentage of modern carbon (MC), determined as per the ASTM Standard D6866-20 Method B, greater than or equal to 50%, more preferentially greater than or equal to 60%, even more preferentially greater than or equal to 70%, advantageously greater than or equal to 80%, typically greater than or equal to 90%

According to a still advantageous embodiment, 100% of the isododecane present in the cosmetic composition comes from the implementation of the method defined hereinabove.

Preferentially, according to such embodiment, the isododecane present in the cosmetic composition of the invention has a percentage of modern carbon (MC), determined as per the ASTM standard D6866-20 Method B, equal to 100%.

The composition according to the invention further comprises at least one compound chosen from: waxes, oils, film-forming agents, dyes and mixtures thereof.

According to an advantageous embodiment, at least 80% by mass of the compounds present in the composition are natural, preferentially at least 90% by mass, more preferentially at least 95% by mass, with respect to the total mass of the composition.

Preferentially, at least 50% by mass of the compounds present in the composition, other than isododecane, are natural, preferentially at least 80% by mass, more preferentially at least 90% by mass, advantageously at least 95% by mass, with respect to the total mass of compounds distinct from isododecane and present in the composition.

Preferentially, the cosmetic composition according to the invention has a percentage of modern carbon (PMC), determined as per the ASTM Standard D6866-20 Method B, greater than or equal to 65%, more preferentially greater than or equal to 75%, even more preferentially greater than or equal to 80%, typically greater than or equal to 85%.

Advantageously, the cosmetic composition according to the invention has a percentage of modern carbon (PMC), determined as per the ASTM standard D6866-20 Method B, greater than or equal to 90%, more advantageously greater than or equal to 95%.

Advantageously, the cosmetic composition according to the invention has a percentage of modern carbon (MC), determined as per the ASTM Standard D6866-20 Method B, greater than or equal to 90%, preferentially greater than or equal to 95%, more preferentially greater than or equal to 99%, typically equal to 100%.

"Wax" as defined by the invention refers to a substance which contributes to giving the products into which same are introduced, perfect adhesion to the skin surface and which forms a protective film resistant to the action of detergents.

Wax(es) can come from animals, plants or minerals.

Preferentially, the wax(es) are chosen from plant or animal waxes.

An example of animal wax is beeswax.

Examples of plant waxes of plant include carnauba wax or rice wax.

Preferentially, the composition according to the invention comprises from 2 to 60% by mass of waxes, with respect to the total mass of the composition.

"Oil" as defined by the invention refers to a fatty and flammable substance, liquid at ambient temperature and pressure, insoluble in water and having a density of less than 1.

The oil(s) can come from plants, animals or minerals.

Preferentially, the oil(s) are chosen from plant oils.

Plant oils include castor oil, jojoba oil (*Simmondsia chinensis*), apricot kernel oil, coconut oil, sweet almond oil, *camellia* oil, broccoli oil, macadamia oil, plum oil or octyldodecanol.

Preferentially, composition according to the invention comprises from 1 to 40% by mass of oils, with respect to the total mass of the composition.

"Film-forming agent" as defined by the invention refers to a compound apt to produce a continuous film on the skin, the hair and/or the nails.

Preferentially, the film-forming agent(s) are chosen from resins, gums and mixtures thereof.

Resins and gums are natural components. Gums are soluble in water, unlike resins.

Gum(s) can come from plants or animals.

Plant gums include Gum Arabic.

Animal gums include in particular shellac or further xanthan gum.

Resin(s) can come from plants or animals.

Preferentially, the resin or resins are chosen from plant resins.

Plant resins include sal tree resin (*Shorea robusta*).

Preferentially, the composition according to the invention comprises from 2 to 40% by mass of film-forming agent(s), with respect to the total mass of the composition.

"Dye" as defined by the invention refers to a coloring chemical substance.

The dye or dyes can come from plants, animals, minerals or can be synthetic dyes.

Preferentially, the dye or dyes are chosen from plant dyes, animal dyes or mineral dyes.

Plant dyes include in particular plant and/or fruit extracts containing coloring substances.

Animal dyes include in particular carmine (CI 75470),

Mineral dyes include in particular titanium dioxide (CI 77891); iron oxides such as e.g. iron trioxide (CI 77491), iron oxide (CI 77492), iron tetraoxide (CI 77499) or further mica, Synthetic dyes include in particular lacquered red 28 (CI 45410), red 7 (CI 15850), eosin (CI 45380), lacquered yellow 5 (CI 19140), lacquered yellow 6 (CI 15985), lacquered blue 1 (CI 42090), carmine (CI 75470), lacquered red 33 (CO 17200), lacquered red 34 (CI 15 880) or further lacquered red 6 (CI 15850).

Preferentially, the composition according to the invention comprises from 0 to 30% by mass of dyes, with respect to the total mass of the composition.

According to an advantageous embodiment, at least 80% by mass of the compounds present in the composition according to the invention are natural, preferentially at least 90% by mass, more preferentially at least 95% by mass, with respect to the total mass of the composition.

According to a preferred embodiment, the composition according to the invention comprises, preferentially consists essentially of:

from 2 to 80% by mass of isododecane,
from 2 to 60% by mass of wax(es)
from 1 to 40% by mass of film-forming agent(s), and
from 0 to 30% by mass of dye(s),
the percentages being expressed with respect to the total mass of the composition.

According to one embodiment, the cosmetic composition according to the invention further comprises one or a plurality of butter(s).

"Butter" as defined by the invention, refers to a fatty and flammable substance, solid at ambient temperature and pressure, insoluble in water and having a density of less than 1.

The butter or butters can be chosen from butters coming from plants, animals, or further synthetic butters.

Preferentially, the butter or butters are chosen from butters coming from plants or animals, more preferentially from plant oils.

Plant butters include shea butter, *camellia* butter and coconut butter.

Preferentially, the composition according to the invention comprises from 1 to 40% by mass of butter(s), with respect to the total mass of the composition.

According to one embodiment, the cosmetic composition according to the invention further comprises one or a plurality of emulsifiers.

"Emulsifier" as defined by the invention, refers to a surfactant compound apt to stabilize an emulsion.

Preferentially, the emulsifier(s) are chosen from natural emulsifiers.

Natural emulsifiers include in particular lecithin, either from plants or animals; monoglycerides and diglycerides of fatty acids and mixtures thereof.

Preferentially, the composition according to the invention comprises from 0 to 10% by mass of emulsifier(s), with respect to the total mass of the composition.

The cosmetic composition according to the invention can further comprise other additives which are usual in the field, such as e.g. antioxidants. Such compounds are well known to a person skilled in the art.

According to a first variant, the cosmetic composition according to the invention is anhydrous.

According to a second variant, the cosmetic composition according to the invention comprises water.

Preferentially, according to the second variant, the composition according to the invention is in the form of an emulsion, in particular in the form of an oil-in-water or water-in-oil emulsion.

According to a first variant, the composition according to the invention comprises at least one dye, preferentially chosen from pigments.

Preferentially, according to such variant, the composition according to the invention is a make-up composition.

Preferentially, the make-up composition according to the invention consists of a foundation; a mascara; a solid or liquid eyebrow mascara; an eyebrow pencil; a blusher; a corrector; a solid or liquid lipstick; an eyeshadow; an eyeliner or a primer, in particular a pearly primer.

Preferentially, when the make-up composition is chosen from foundations, same comprises:

0 to 10% by mass of emulsifier(s)
from 5 to 40% by mass of isododecane,
from 5 to 40% by mass of wax(es)
from 3 to 40% by mass of oil(s)
from 2 to 20% by mass of film-forming agent(s), and
from 5 to 20% by mass of dye(s),
the percentages being expressed with respect to the total mass of the composition.

Preferentially, when the make-up composition is chosen from either liquid or solid eyebrow mascaras and mascaras, same comprises:

0 to 10% by mass of emulsifier(s)
from 2 to 80% by mass of isododecane,
from 5 to 60% by mass of wax(es)
from 3 to 30% by mass of film-forming agent(s),
from 2 to 20% by mass of butter(s) and
from 5 to 20% by mass of dye(s),
the percentages being expressed with respect to the total mass of the composition.

Preferentially, when the make-up composition is chosen from blushers, same comprises:

from 2 to 80% by mass of isododecane,
from 5 to 60% by mass of wax(es)
from 2 to 30% by mass of film-forming agent(s),
from 3 to 40% by mass of oil(s)
from 2 to 20% by mass of butter(s) and
from 1 to 20% by mass of dye(s),
the percentages being expressed with respect to the total mass of the composition.

Preferentially, when the make-up composition is chosen from liquid lipsticks, same comprises:

from 2 to 60% by mass of isododecane,
from 5 to 40% by mass of wax(es)
from 5 to 40% by mass of oil(s)
from 2 to 30% by mass of film-forming agent(s),
from 2 to 20% by mass of butter(s) and
from 3 to 25% by mass of dye(s), the percentages being expressed with respect to the total mass of the composition.

Preferentially, when the make-up composition is chosen from solid lipsticks, same comprises:

from 2 to 60% by mass of isododecane, from 5 to 60% by mass of wax(es)

from 5 to 40% by mass of oil(s)

from 2 to 30% by mass of film-forming agent(s), from 2 to 20% by mass of butter(s) and from 3 to 25% by mass of dye(s), the percentages being expressed with respect to the total mass of the composition.

Preferentially, when the make-up composition is chosen from eyeshadows, same comprises:

from 5 to 40% by mass of isododecane, from 2 to 20% by mass of wax(es)

from 5 to 40% by mass of oil(s)

from 2 to 20% by mass of film-forming agent(s), from 2 to 20% by mass of butter(s) and from 3 to 20% by mass of dye(s), the percentages being expressed with respect to the total mass of the composition.

Preferentially, when the make-up composition is chosen from eyeliners, same comprises:

from 2 to 80% by mass of isododecane, from 5 to 60% by mass of wax(es)

from 2 to 30% by mass of film-forming agent(s), from 1 to 10% by mass of oil(s)

from 2 to 20% by mass of butter(s) and from 3 to 25% by mass of dye(s), the percentages being expressed with respect to the total mass of the composition.

Preferentially, when the make-up composition is chosen from primers, same comprises:

from 20 to 90% by mass of isododecane, from 0 to 5% by mass of wax(es)

from 2 to 30% by mass of film-forming agent(s), from 0 to 30% by mass of oil(s)

from 1 to 10% by mass of butter(s) and from 0 to 10% by mass of dye(s), the percentages being expressed with respect to the total mass of the composition.

Advantageously, the make-up composition according to the invention has a resistance over time of greater than or equal to 6 hours, preferentially greater than or equal to 8 hours.

"Resistance" as defined by the invention refers to the resistance of a make-up composition starting from the application thereof to the skin.

Advantageously, the make-up composition according to the invention is water-resistant ("waterproof effect")

According to a second variant, the composition according to the invention is a make-up removing oil.

Preferentially, when the cosmetic composition according to the invention is chosen from make-up removing oils, same comprises:

from 2 to 93% by mass of isododecane, from 1 to 10% by mass of wax(es)

from 2 to 30% by mass of film-forming agent(s), from 1 to 40% by mass of oil(s)

from 2 to 20% by mass of butter(s) and from 1 to 20% by mass of dye(s), the percentages being expressed with respect to the total mass of the composition.

The examples below illustrate the invention.

EXAMPLES

Step 1: Producing Isobutene by Fermentation

Isobutene is produced by biosynthesis using the genetically modified *Escherichia coli* strain MG1655 as described in the example 12 of WO2017085167 and by implementing the method described in the example 1 of WO 2014/086781.

Step 2: Oligomerization of Isobutene to Isododecene

The isobutene obtained at the end of step 1 is introduced into a fixed-bed reactor containing 1.5 g of an Amberlyst™ 35 catalyst. Isooctene, produced during a previous isobutene oligomerization reaction under the same conditions as hereinafter, is also introduced into the reactor. The isobutene/isooctene mass ratio is 66/34, and the total flow rate is 97.5 g/h.

The pressure in the reactor is set at 20 bar, and the setpoint temperature is 90° C. At the reactor outlet, the mixture is flashed so as to remove the unreacted isobutene and isooctene. 53% of the input stream is recovered as a distillate. 47% of the input stream is recovered as a residue.

The mass percentage composition of the residue is as follows:

Isobutene: less than 0.1%,

C4 to C7 alkenes: 0.3%

Isooctene: 5%

Isododecene: 80%

Isohexadecene: 12%

Alkenes with more than 16 carbons: 0.4% with respect to the total mass of the residue, the remainder consisting of impurities.

The mass percentage composition of the distillate is as follows:

Isoobutene: 15%

C4 to C7 alkenes: 1%

Isooctene: 78%

Isododecene: 3%

Isohexadecene: 0%

Alkenes with more than 16 carbons: 0% with respect to the total mass of the distillate, the remainder being impurities.

The residue is distilled for purifying isododecene. The purified mixture then contains 2% by mass of isooctene and 97% by mass of isododecene.

Step 3: Hydrogenation of Isododecene to Isododecane

The purified mixture obtained at the end of step 2 is then introduced successively into two hydrogenation reactors with a flow rate of 23.4 g/h, at 150° C. and under a pressure of 30 bar. The first reactor contains 10 g of a palladium catalyst supported on alumina comprising 0.5% by mass of palladium. The second reactor contains 40 g of the same catalyst. A hydrogen stream at 1.5 eq. is further introduced into the reactor.

The degree of conversion of alkenes into alkanes is greater than 99%.

The product obtained contains more than 96% by mass of isododecane.

The concentration of carbon 14 in isododecane is then measured by the method B, as described in the ASTM D6866-20 standard.

Isododecane has a percentage of modern carbon (PMC) equal to 100%.

Step 4: Preparing a Cosmetic Composition

A mascara cosmetic composition is then prepared from the isododecane obtained at the end of step 3.

The constituents of the composition are given in Table 1 below, the concentrations being expressed by mass percentage, with respect to the total mass of the composition.

TABLE 1

| Phase | Ingredient | Concentration (% by mass) |
|---|---|---|
| A | Beeswax | 13% |
| | Carnauba wax | 15% |
| | Sal tree resin | 10% |
| | Shea butter | 16% |
| B | Isododecane | 38% |
| C | Black iron oxide | 7.5% |
| | Tocopherol | 0.5% |

The composition is prepared by mixing the above-defined constituents under stirring and at a temperature of 85° C., the isododecane being added last. The mixture is then brought to ambient temperature under stirring.

A homogeneous mascara composition is thus obtained.

The invention claimed is:

1. A method for preparing a cosmetic composition comprising:

1) Producing isobutene by a fermentation method comprising the formation of 3-hydroxy-3-methylbutyric acid and/or 3-methylcrotonic acid as an intermediate substance, 2) Converting isobutene to isododecane, and 3) Mixing isododecane with at least one compound selected from: waxes, oils, resins, dyes and mixtures thereof;

wherein step 2) is carried out by oligomerization of isobutene in the presence of isooctene to produce a reaction medium, followed by a hydrogenation step;

wherein isooctene in the reaction medium is separated from the reaction medium and used for a next iteration of said method; and wherein step 2) further comprises a distillation step performed before the hydrogenation step.

2. The method according to claim 1, wherein the oligomerization step is carried out at a pressure ranging from 10 to 30 bar.

3. The method according to claim 1, wherein the oligomerization reaction is carried out at a temperature ranging from 50 to 150° C.

* * * * *